United States Patent [19]

Murphy et al.

[11] Patent Number: 5,049,376

[45] Date of Patent: Sep. 17, 1991

[54] COSMETIC POWDER BAR COMPOSITION AND PROCESS FOR MAKING SAME

[75] Inventors: John H. Murphy, Belle Mead; Hovig O. Ounanian, Princeton Junction; Kenneth A. Cohen, Aberdeen; Joseph DiSomma, Ramsey; Harvey Gedeon, Allendale, all of N.J.

[73] Assignee: Revlon, Inc., New York, N.Y.

[21] Appl. No.: 470,921

[22] Filed: Jan. 26, 1990

[51] Int. Cl.$^5$ ............................................... A61K 7/02
[52] U.S. Cl. ........................................ 424/63; 424/69; 424/83; 424/DIG. 5
[58] Field of Search ............... 424/63, 64, 69, 83, 424/DIG. 5; 514/844; 132/216, 218, 320

[56] References Cited

U.S. PATENT DOCUMENTS

| | | | |
|---|---|---|---|
| 3,800,034 | 3/1974 | Kircher et al. | 424/63 |
| 4,190,455 | 2/1980 | Bijen et al. | 106/722 |
| 4,379,136 | 4/1983 | Mochida | 424/63 X |
| 4,540,439 | 9/1985 | Kurandt | 106/783 |
| 4,591,502 | 5/1986 | Schlossman | 424/63 |
| 4,605,553 | 8/1986 | Passalacqua | 424/59 |
| 4,624,273 | 11/1986 | Carr | 132/216 |
| 4,659,571 | 4/1987 | Laba | 424/65 |
| 4,669,492 | 6/1987 | von Kleinsorgen | 132/218 |
| 4,724,138 | 2/1988 | Duffy et al. | 424/63 |
| 4,748,991 | 6/1988 | Hofman et al. | 132/320 |

*Primary Examiner*—Thurman K. Page
*Assistant Examiner*—Susan S. Rucker
*Attorney, Agent, or Firm*—Julie Blackburn

[57] ABSTRACT

A cosmetic powder bar composition is disclosed. The composition, substantially oil free, comprises calcium sulfate dihydrate, mica or mica-containing composite material and polyethylene. A unique process for making this composition is also set forth. In this process a powder phase composition and a liquid phase composition are separately prepared. The two compositions are contacted to form a slurry. The slurry is placed in molds and heated to remove free water therefrom.

10 Claims, No Drawings

COSMETIC POWDER BAR COMPOSITION AND PROCESS FOR MAKING SAME

BACKGROUND OF THE INVENTION

1. Field of the Invention

The solidification of cosmetic powders to produce pressed powder compositions is representative of a growing trend in the cosmetic arts. This growth in pressed powder compositions can be ascribed to at least two advantages that result from such packaging. For one thing, a solidified powder is portable. The user is likewise advantaged in that it can be applied without the messiness associated with loose powder. Indeed, certain cosmetic pressed powders, e.g., eyeshadows, blushes and the like, are presently available as solidified powders. That is, finely divided loose powders are placed into gaudets, i.e. pans, and under high pressure are pressed into cakes.

Although pressed powders provide the above discussed advantages they possess one detrimental characteristic. That is, the powder constituents do not bind with each other to form a solid. Thus, a binder, usually in liquid form, is added to provide this missing binding property. The use of one or more binders, however, is detrimental to users of cosmetic compositions who have oily skin. In order to provide beauty enhancement users who have oily skin require cosmetics which reduce, rather than increase, the oil level of surface layers of the skin. Certainly, the use of a cosmetic composition laden with oily binder decreases, rather than increases, the product's beauty enhancement to a user having an oily or even normal skin.

Another detrimental property associated with cosmetic powder compositions, which are usually pressed powders, is that, by containing high concentrations of oily binder, they obviously do not contain water soluble but oil insoluble humectants and other like moisturizing agents. The inclusion of moisturizing agents in cosmetic products is highly desirable in that these agents provide a soft comfortable feel to the skin.

2. Background of the Prior Art

A particularly pertinent disclosure of a powder composition is embodied in U.S. Pat. No. 4,724,138 to Duffy et al. Duffy et al. describes a method for forming a pigmented cosmetic powdered powder product which comprises blending a powder phase composition, which includes a powdered pigment and calcium sulfate hemihydrate, with an aqueous phase comprising water and a surfactant at elevated temperature, i.e., about 60° C. The product of this combination is poured into a mold and allowed to set. The product is removed from the mold and dried at very high temperature, in excess of 128° C., to produce a solid employed primarily in cosmetic stick products.

This high heat treatment prevents the cosmetic product from having the "feel" deemed attractive to users. That is, the product is not soft due to the high curing temperature and the resultant driving off of many cosmetically acceptable humectants which evaporate at these high processing temperatures.

U.S. Pat. No. 4,624,273 to Carr, another relevant reference, discloses a cosmetic pigmented pencil. The pencil of the Carr patent comprises a core consisting of a water-set mixture of plaster of paris, mica or other laminar material and pigment or color. The cosmetic composition disposed in the pre-formed core may also include preservatives and bacteriostats.

As in Duffy et al., the Carr patent does not address the need in the art for a free standing solid possessing high payoff. Rather than producing a free standing powder product, Carr is limited to a cosmetic pencil.

BRIEF SUMMARY OF THE INVENTION

A new cosmetic composition has now been developed which not only permits the inclusion of humectants and moisturizing agents but which is substantially free of oils. In this way, a novel cosmetic powder bar composition has been developed which overcomes the problems of high oil concentration and the absence of moisturizing agents characteristic of cosmetic powder bars of the prior art.

In accordance with the present invention a cosmetic powder bar composition is provided. The composition comprises the calcium sulfate dihydrate, mica or mica-containing composite material and polyethylene.

In further accordance with the present invention a process for making a cosmetic powder bar composition is described. In this process a powder phase composition, comprising a mixture of calcium sulfate hemihydrate, mica or mica-containing composite material and polyethylene, is formed by blending these solid components. A liquid phase composition, which includes water, is provided. The powder phase and the liquid phase are combined to form a slurry. The thus formed slurry is poured into molds at ambient conditions. The slurry in molds is then heated at a temperature in the range of between about 20° C. and about 70° C. until dry.

DETAILED DESCRIPTION

The composition of the present invention, a cosmetic powder bar composition, comprises a plurality of powdered components, the most critical of which is calcium sulfate dihydrate. Those skilled in the art are aware that calcium sulfate dihydrate has the structural formula $CaSO_4.2H_2O$. It is emphasized that calcium sulfate dihydrate is distinguished from calcium sulfate hemihydrate which has the structural formula $(CaSO_4)_2.H_2O$. The hemihydrate can be converted into the dihydrate by reacting the hemihydrate with water. Specifically, three moles of water are reacted with one mole of the hemihydrate to produce two moles of the calcium sulfate dihydrate. This conversion reaction is discussed hereinafter.

The calcium sulfate dihydrate constituent uniquely provides bindability to the cosmetic powder bar composition. As such, it serves the function provided in prior art free standing cosmetic powder bar compositions by oil-based binders. Its use thus not only eliminates the requirement that the cosmetic powder bar composition include high oil concentration but permits the inclusion of water-soluble humectants in the composition. The desirable inclusion of humectants is considered in the discussion of that component.

The calcium sulfate dihydrate is preferably present in the cosmetic powder bar composition in a concentration in the range of between about 20% and about 40% by weight, based on the total weight of the powder bar composition. More preferably, the calcium sulfate dihydrate represents between about 22% and about 28% by weight, based on the total weight of the cosmetic powder bar composition. Still more preferably, the calcium sulfate dihydrate component is representative of between about 23% and about 25% by weight, based on the total weight of the composition.

A second critical component of the cosmetic powder bar composition is mica or mica-containing composite materials. The mica component contemplated for use in the present application is that ingredient recited as mica, including those materials recited thereunder as materials containing mica, in the CTFA Cosmetic Ingredient Dictionary, Third Edition, published by the Cosmetic, Toiletry and Fragrance Association, Inc., Washington, D.C. (1982), which text is incorporated herein by reference.

This essential component is usually present in a concentration in the range of between about 16% and about 37% by weight, based on the total weight of the composition. Preferably, the concentration of the mica component is in the range of between about 19% and about 35% by weight, again based on the total weight of the cosmetic powder bar composition. Even more preferably, the mica concentration, based on the total weight of the powder bar composition, is in the range of between about 22% and about 29% by weight.

The mica component is crucial to providing high pay-off, an essential property of a solid cosmetic powder product. That is, the laminar or planar nature of the mica particles allows high levels of pick up when an applicator is drawn over the bar.

Yet a third critical ingredient in the cosmetic powder bar composition is polyethylene.

The polyethylene component of the cosmetic powder bar composition is preferably present in a concentration in the range of between about 0.5% and about 24% by weight, based on the total weight of the composition. More preferably, the cosmetic powder bar composition includes between about 5% and about 15% by weight polyethylene, based on the total weight of the composition. Still more preferably, between about 7% and about 13% by weight of the cosmetic powder bar composition is polyethylene.

The polyethylene component provides the requisite texture to the solidified powder cosmetic product insuring its structural integrity. That is, the incorporation of polyethylene eliminates any chance that the composition will be friable. As such, the composition is free of powderiness and the like.

In addition to the above essential ingredients of the cosmetic powder bar composition, there are several other components that may be included therein to insure its effectiveness as a cosmetic product. One such preferred component of the cosmetic powder bar composition is talc. The talc component of the cosmetic powder bar composition is the material denoted by that name in the CTFA Cosmetic Ingredient Dictionary, Third Edition, incorporated herein by reference.

It is preferred that the talc component, if present, be included in a concentration in the range of between about 0.1% and about 16% by weight, based on the total weight of the composition. More preferably, the talc concentration is in the range of between about 4% and about 12% by weight, based on the total weight of the cosmetic powder bar composition. Still more preferably, the concentration by weight of the talc component in the cosmetic powder bar composition is in the range of between about 6% and about 10%.

The talc component is included for its positive "feel" effect. What is meant by this is that the inclusion of talc provides a silky feel to the skin upon which it is applied.

Another solid component preferably present in the cosmetic powder bar composition is calcium carbonate. The calcium carbonate contemplated for use in this composition is the product so denoted in the CTFA Cosmetic Ingredient Dictionary, Third Edition, incorporated herein by reference. This component is included to absorb moisture on the skin. By doing so, this component allows the composition to remain on the user's skin for longer periods of time than would otherwise be the case. The absorption of moisture prevents the dissolving or dispersion of the composition on the skin.

To provide this function it is preferred that calcium carbonate be included in the composition in a concentration range, expressed as a percent by weight of the total composition, of between about 1% and about 9.5%. More preferably, calcium carbonate is present in the cosmetic powder bar composition in a concentration in the range of between about 2% and about 8% by weight. Even more preferably, the calcium carbonate concentration by weight as a fraction of the total weight of the composition is in the range of between about 3.5% and about 7%.

In addition to the above components the cosmetic powder bar composition preferably comprises one or more colorants. Cosmetically acceptable colorants are utilized to provide color to highlight and accentuate the presence of the cosmetic powder bar composition on the skin of the user.

Preferred colorants are cosmetically acceptable pigments recited in the aforementioned CTFA Cosmetic Ingredient Dictionary, Third Edition. Among the pigments preferred for use as colorants in the powder bar composition are iron oxides, titanium dioxide, carmine, chromium oxide greens, chromium hydroxide green, ferric ammonium ferrocyanide, ferric ferrocyanide, ultramarine blue, ultramarine violet, ultramarine pink, manganese violet, FD&C Yellow No. 5 aluminum lake, FD&C Yellow No. 6 aluminum lake, FD&C Blue No. 1 aluminum lake, D&C Red No. 7 calcium lake, D&C Red No. 30 lake and mixtures thereof, as defined in said incorporated by reference CTFA Cosmetic Ingredient Dictionary, Third Edition. Of these, iron oxides, titanium dioxide and mixtures thereof are particularly preferred.

The colorant concentration in the composition, expressed in weight concentration terms, is preferably in the range of between about 0.1% and about 22.5%. More preferably, the concentration of colorant in the composition is in the range of between about 2% and about 15% by weight, based on the total weight of the composition. Even more preferably, the colorant concentration is in the range of between about 4% and about 12% by weight, based on the total weight of the cosmetic powder bar composition.

In addition to the above powder phase composition in the formation of the cosmetic powder bar composition, the composition of the present invention also preferably incorporates components that form the liquid phase composition prior to the synthesis of the final cosmetic powder bar composition. Of these liquid components the component present in the highest concentration, expressed as percent by weight based on the total weight of the composition, is a humectant.

All of the multiplicity of cosmetically acceptable humectants, included in the incorporated by reference CTFA Cosmetic Ingredient handbook, First Edition, can be employed in the composition of this invention.

Of this exceedingly large number of cosmetically acceptable humectants, butylene glycol, propylene glycol and glycerin, as defined therein, are more preferred for use in this composition. Of these, glycerin is most preferred.

The concentration of the humectant, preferably glycerin, is usually in the range of between about 1% and about 20% by weight, based on the total weight of the cosmetic powder bar composition. More preferably, the glycerin concentration, expressed in weight percent based on the total weight of the composition, is in the range of between about 4% and about 14%. Yet more preferably, glycerin represents about 7% to about 12% by weight, based on the total weight of the cosmetic powder bar composition.

Another preferred liquid phase component is an emulsifier. An emulsifier permits miscibility between the water and oil soluble components of the powder bar composition. The emulsifier is preferably present in a concentration in the range of between about 0.75% and about 4% by weight, based on the total weight of the composition. More preferably, the concentration of the emulsifier is in the range of between about 1.25% and about 3.25% by weight, again based on the total weight of the composition. Still more preferably, the concentration of the emulsifier is in the range of between about 2% and about 3% by weight based on the total weight of the composition.

Although a multiplicity of emulsifiers may be employed in the composition, a particularly preferred emulsifier is Polysorbate 20, as defined in the CTFA Cosmetic Ingredient Dictionary, Third Edition, incorporated herein by reference.

Yet another ingredient included in the composition of this invention is one or more preservatives. The preservative component, usually included in cosmetic compositions, may be one or more of the parabens, such as methylparaben, ethylparaben, propylparaben and the like, which parabens are defined in the aforementioned CTFA Cosmetic Ingredient Dictionary, Third Edition, incorporated herein by reference. Other preservatives may be alternately or may be additionally included in the cosmetic powder bar composition. For example, the composition preferably incorporates diazolidinyl urea, as defined in the CTFA Cosmetic Ingredient Dictionary, Third Edition, incorporated herein by reference.

The total preservative concentration, incorporating the one or more preservatives included in the composition of this invention, comprises approximately 0.5% to approximately 0.75% by weight, based on the total weight of the composition. More preferably, the preservative component is present in a concentration in the range of between about 0.55% and about 0.65% by weight, based on the total weight of the composition.

A final component which is optionally is present in the cosmetic powder bar composition is a catalyst. The catalyst component serves to accelerate the setting of the cosmetic powder bar as will be explained hereinafter. Preferred species of the catalyst of the composition of the present invention include potassium sulfate and sodium sulfate. Of these, potassium sulfate is particularly preferred.

The catalyst component is representative of a concentration in the range of between 0 and about 0.75% by weight, based on the total weight of the cosmetic powder bar composition. More preferably, the catalyst component is present in an amount in the range of between about 0.35% and about 0.6% by weight, based on the total weight of the composition.

A second aspect of the present invention involves the unique process by which the above-discussed composition is prepared. In the novel process of the present invention separate powder phase and liquid phase compositions are formulated.

Turning first to the powder phase composition, that composition incorporates calcium sulfate hemihydrate, mica and polyethylene. The first mentioned component is preferably present in an amount such that the calcium sulfate hemihydrate concentration is in the range of between about 20% and about 45% by weight, based on the total weight of the powder composition. More preferably, the concentration of the calcium sulfate hemihydrate is in the range of between about 24% and about 34% by weight of the powder composition. Still more preferably, the concentration of the calcium sulfate hemihydrate is in the range of between about 26% and about 30% by weight, based on the total weight of the powder phase composition.

The mica constituent is preferably representative of between about 15% and about 50% by weight of the total weight of the powder phase composition. More preferably, the mica constituent is about 25% to about 40% by weight of the powder phase composition. Yet more preferably, the mica concentration is in the range of between about 28% and about 32% by weight, based on the total weight of the powder phase composition.

The third essential ingredient of the powder phase composition, polyethylene, is preferably present therein in a concentration in the range of between about 5% and about 30% by weight, based on the total weight of the powder phase composition. More preferably, polyethylene comprises between about 8% and about 20% by weight of the powder phase composition. Still more preferably, the polyethylene constituent is representative of between about 10% and about 15% by weight, based on the total weight of the powder phase composition.

The powder phase composition, in a preferred embodiment, includes additional components. Among these components is talc. The talc component is representative of between about 3% and about 28% by weight, based on the total weight of the powder phase composition. More preferably, talc is present in an amount in the range of between about 6% and about 18% by weight of the powder phase composition. Most preferably, talc comprises between about 8% and about 12% by weight of the powder phase composition.

Another preferred constituent of the powder phase is calcium carbonate. Calcium carbonate is preferably included in this phase in an amount in the range of between about 2% and about 10% by weight, based on the total weight of the powder phase composition. More preferably, the calcium carbonate constituency of the powder phase composition, expressed in percentage by weight, is in the range of between about 4% and about 8%.

Yet another preferred constituent of the powder phase composition is one or more colorants. The one or more solid colorants preferably included in the powder phase composition is representative of between about 5% and about 30% by weight of the powder phase composition. More preferably, the colorant component or components is representative of between about 7% and about 20% by weight of the powder phase composition. In an even more preferred embodiment, the colorant comprises between about 9% and about 14% by weight of the powder phase composition. In a particular preferred embodiment of the powder phase composition the colorant constituents therein are titanium dioxide, iron oxide red, iron oxide yellow and iron oxide black.

In addition to the above components the powder phase composition may optionally include a solid phase preservative. As is mentioned below, in preferred embodiments of the process of the present invention one or more preservatives are oftentimes included in the liquid phase composition. In the preferred embodiment where at least one preservative is included in the powder phase composition, it is present in an amount in the range of between about 0.1 to 1% by weight. If present, it is preferably propylparaben.

As stated above, a liquid phase composition is prepared separately from the above-discussed powder phase composition in the process of the present invention. The liquid phase composition incorporates, as its major constituent, water, in an amount that ranges from between about 60% and about 95% by weight, based on the total weight of the water phase composition. Preferably, the concentration of water is in the range of between about 75% and about 92% by weight of the liquid phase composition. Still more preferably, the water constituent is representative of between about 80% to about 90% by weight of the liquid phase composition.

Another preferred component of the liquid phase composition is a humectant, preferably, glycerin. The humectant, usually glycerin, component is present in a concentration in the range of between about 1% and about 20% by weight, based on the total weight of the liquid phase composition. More preferably, the humectant constituent is representative of between about 5% and about 14% by weight of the liquid phase composition. Most preferably, the humectant constituent constitutes between about 8% and about 11% of the total weight of the liquid phase composition.

An emulsifier is usually included in the liquid phase composition. When present, the emulsifier is preferably provided in a concentration in the range of between about 1% and about 5% by weight. More preferably, the liquid phase composition comprises between about 2% and about 4% by weight of the liquid phase composition. Most preferably, between about 2.5% and about 3.5% by weight, based on the total weight of the liquid phase composition is the emulsifier. As stated earlier, the preferred emulsifier of the liquid phase composition is Polysorbate 20.

The liquid phase composition also preferably includes one or more preservatives. In the preferred embodiment wherein a preservative is included in the liquid phase composition, it is preferably present in a concentration in the range of between about 0.1% to about 1% by weight, based on the total weight of the liquid phase composition. More preferably, this concentration is in the range of between about 0.25% and about 0.75% by weight. Most preferably, the preservative constituent is representative of between about 0.4% and about 0.6% by weight based on the total weight of the liquid phase composition.

It should be appreciated that the preservative constituent of the liquid phase composition may be provided by one or more ingredients. In a preferred embodiment, two preservatives, methylparaben and ethylparaben, are utilized in the liquid phase composition. It is emphasized that the presence of at least one preservative constituent in the liquid phase composition is independent of the inclusion of a preservative in the powder phase composition.

A last constituent that may be included in the liquid phase composition is a catalyst. Preferred catalysts for this application are potassium sulfate or sodium sulfate. Potassium sulfate is the more preferred choice as the catalyst of the liquid phase composition. Independent of its identity, the catalyst, if present, is representative of between about 0.01% and about 1.00% by weight in the liquid phase composition.

In the next step in the process of forming the cosmetic powder bar composition, the two separately prepared compositions, the powder phase composition and the liquid phase composition, are contacted. This contact occurs by mixing the two compositions. Preferably, the powder phase composition is mixed with the liquid phase composition in a powder phase composition to liquid phase composition weight ratio in the range of between about 3:5 and 5:3. More preferably, this weight ratio of powder to liquid phase compositions is in the range of between about 4:5 and about 5:4. Most preferably, the amount of powder phase composition to liquid phase composition contacted in this step of the process is in the range of between about 43:57 and about 45:55.

The powder phase composition and liquid phase composition are mixed together under agitation at room temperature to form a slurry. The slurry is poured into molds shaped in accordance with the desired shape of the free-standing cosmetic powder bar composition. The slurry is allowed to set in the mold for approximately one hour. The set slurry in molds is thereupon transferred to a heated environment, usually an oven, maintained at a temperature in the range of between about 40° C. and about 70° C., more preferably, between about 50° C. and 65° C. The molds containing the set slurry remain in this heated environment for at least 18 hours. The actual time may exceed 18 hours if the cosmetic powder bar product in the molds requires more time to reach the minimum degree of drying required. It is emphasized that the minimum degree of drying required of the final cosmetic powder bar composition is no more than 5% by weight free water.

Although the invention is independent of any theory explaining the mechanism of the above described process, it is theorized that water included in the liquid phase composition reacts with the calcium sulfate hemihydrate constituent of the powder phase composition to form calcium sulfate dihydrate. Thus, although there are water molecules in the cosmetic powder bar composition, none of these are free water molecules. These water molecules are tied up as part of the dihydrate molecule.

It is noted that the presence of a catalyst accelerates the reaction of calcium sulfate hemihydrate to calcium sulfate dihydrate at ambient conditions. It is furthermore emphasized that any more than 5% by weight excess free water, i.e., water present in excess of that stoichiometrically required in this reaction, is driven off in the heating step.

The following examples are given to illustrate the scope of the present invention. Because these examples are given for illustrative purposes only, the invention should not be limited thereto.

EXAMPLE 1

Preparation of a Powder Phase Composition

A mixing container provided with agitation was charged with the following solid components, wherein parts denotes parts by weight: 6.4 parts calcium carbonate, 9.6 parts titanium dioxide, 0.72 part iron oxide red, 1.0 part iron oxide yellow, 0.12 part iron oxide black and 0.06 part propylparaben. These solid components were mixed, pulverized and passed through an 0.02 inch screen. The resultant product was a color powder mixture.

A second solid mixture was prepared in a blender by adding 31.3 parts mica, 12.7 parts polyethylene, 27.6 parts calcium sulfate hemihydrate and 10.5 parts talc therein. It should be appreciated that parts again mean parts by weight. The solid components were blended until a uniform solid mixture was obtained.

Upon obtaining a uniform mixture, the solid color powder mixture in the mixing container was added to this second solid mixture in the blender and the two solid mixtures were blended together until a uniform powder phase composition was obtained.

EXAMPLE 2

Preparation of a Liquid Phase Composition

A tank provided with a propeller type agitation was charged with 9.46 parts glycerin, 0.24 part methylparaben and 0.10 part ethylparaben. Again, all parts recited are parts by weight. These ingredients were mixed until the methylparaben and the ethylparaben were completely dissolved in the glycerin.

In a larger tank, also provided with propeller type agitation, 86.77 parts of water were introduced. The charging into the tank of the water corresponded to the introduction of agitation therein. After all the water had been charged into the main tank, 0.54 part potassium sulfate, 2.70 parts Polysorbate 20 and 0.19 part diazolidinyl urea were added thereto. Mixing continued until all the solids were dissolved in the water. At this point the solution of glycerin, methylparaben and ethylparaben was added to the contents of the larger tank. The two liquid solutions were then mixed together to provide a uniform liquid phase composition.

EXAMPLE 3

Preparation of a Cosmetic Color Bar Composition 44.5 Parts by weight of the powder phase composition, formed in accordance with Example 1, were combined with 55.5 parts by weight of the liquid phase composition, produced in Example 2, at ambient conditions. The two compositions were mixed until a uniform slurry was obtained. Upon obtaining a uniform slurry, the slurry was poured into molds and allowed to set for one hour at ambient conditions. Thereupon, the molds were transferred into an oven maintained at a temperature in the range of between about 50° C. and about 55° C. The slurry, maintained in the molds, was held in the oven for about 18 hours. Upon removal from the oven a dry cosmetic powder bar composition was formed in each of the molds.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A cosmetic powder bar composition comprising about 20% to about 40% calcium sulfate dihydrate, about 16% to about 37% mica or mica-containing composite material, and about 0.5% to about 2.4% polyethylene, about 0.5% to about 16% talc, about 1% to about 9.5% calcium carbonate, about 1% to about 20% humectant, about 0.75% to about 4% emulsifier, about 0.1% to about 22.5% colorant, about 0.5% to about 0.75% preservative, and about 0 to about 0.75% of a catalyst which accelerates the reaction of calcium sulfate hemihydrate to calcium sulfate dihydrate at ambient conditions, all said concentrations by weight of the total composition.

2. A composition in accordance with claim 1 wherein said composition comprises between about 22% and about 28 by weight calcium sulfate dihydrate, between about 19% and about 35% by weight mica or mica-containing composite material and between about 5% and about 15% by weight polyethylene.

3. A composition in accordance with claim 2 wherein said composition comprises between about 23% and about 25% by weight calcium sulfate dihydrate, between about 22% and about 29% by weight mica or mica-containing composite material and between about 7% and about 13% by weight polyethylene.

4. A composition in accordance with claim 1 wherein said humectant is glycerin.

5. A composition in accordance with claim 4 wherein said colorant component is selected from the group consisting of iron oxides, titanium dioxide, carmine, chromium oxide greens, chromium hydroxide green, ferric ammonium ferrocyanide, ferric ferrocyanide, ultramarine blue, ultramarine violet, ultramarine pink, manganese violet, FD&C Yellow No. 5 aluminum lake, FD&C Yellow No. 6 aluminum lake, FD&C Blue No. 1 aluminum lake, D&C Red No. 7 calcium lake, D&C Red No. 30 lake and mixtures thereof.

6. A composition in accordance with claim 5 wherein said colorant component is selected from the group consisting of iron oxides, titanium dioxide and mixtures thereof.

7. A composition in accordance with claim 5 wherein said emulsifier is Polysorbate 20.

8. A composition in accordance with claim 7 wherein said preservative component comprises methylparaben, ethylparaben, propylparaben and diazolidinyl urea.

9. A composition in accordance with claim 4 wherein said composition comprises between about 4% and about 12% talc, between about 2% and about 8% calcium carbonate and between about 4% and about 14% glycerin, said percentages being by weight based on the total weight of the composition.

10. A cosmetic powder bar composition comprising between about 23% and about 25% calcium sulfate dihydrate, between about 22% and about 29% mica, between about 7% and about 13% polyethylene, between about 6% and about 10% talc, between about 3.5% and about 7% calcium carbonate, between about 7% and about 12% glycerin, between about 2% and about 3% Polysorbate 20, between about 4% and about 12% colorant, said colorant including titanium dioxide and iron oxides and between about 0.55% and about 0.65% preservative, said preservative including diazolidinyl urea, methylparaben, ethylparaben and propylparaben, said percentages being by weight based on the total weight of the composition.

* * * * *